(12) United States Patent
Housman

(10) Patent No.: US 9,155,531 B2
(45) Date of Patent: Oct. 13, 2015

(54) MINIATURIZED DUAL DRIVE OPEN ARCHITECTURE SUTURE ANCHOR

(71) Applicant: Smith & Nephew, Inc., Andover, MA (US)

(72) Inventor: Mark Edwin Housman, North Attleborough, MA (US)

(73) Assignee: Smith & Nephew, Inc., Memphis, TN (US)

( * ) Notice: Subject to any disclaimer, the term of this patent is extended or adjusted under 35 U.S.C. 154(b) by 0 days.

(21) Appl. No.: 13/838,942

(22) Filed: Mar. 15, 2013

(65) Prior Publication Data

US 2014/0277130 A1    Sep. 18, 2014

(51) Int. Cl.
*A61B 17/04*     (2006.01)
*A61B 17/88*     (2006.01)
*A61B 17/86*     (2006.01)
*A61F 2/08*      (2006.01)

(52) U.S. Cl.
CPC ............ *A61B 17/0401* (2013.01); *A61B 17/869* (2013.01); *A61B 17/8877* (2013.01); *A61B 17/888* (2013.01); *A61B 2017/0409* (2013.01); *A61B 2017/0441* (2013.01); *A61B 2017/0445* (2013.01); *A61B 2017/0448* (2013.01); *A61B 2017/0458* (2013.01); *A61F 2/0811* (2013.01); *A61F 2002/0841* (2013.01); *A61F 2002/0852* (2013.01); *A61F 2230/0021* (2013.01)

(58) Field of Classification Search
CPC ............. A61B 17/0401; A61B 17/869; A61B 17/8877; A61B 2017/0409; A61B 2017/0411; A61B 2017/0414; A61B 2017/044; A61B 2017/0441; A61B 2017/0445; A61B 2017/0446; A61B 2017/0448; A61B 2017/0458; A61F 2/0811; A61F 2002/0817; A61F 2002/0841
USPC .......................................................... 606/232
See application file for complete search history.

(56) References Cited

U.S. PATENT DOCUMENTS

| | | | |
|---|---|---|---|
| 3,499,222 | A | 3/1970 | Linkow et al. |
| 3,869,942 | A | 3/1975 | DeCaro |
| 4,177,797 | A | 12/1979 | Baylis et al. |

(Continued)

FOREIGN PATENT DOCUMENTS

| | | |
|---|---|---|
| CN | 1829479 A | 9/2006 |
| CN | 101031248 A | 9/2007 |

(Continued)

OTHER PUBLICATIONS

International Search and Written Opinion for PCT/US2014/033535 mailed Jul. 18, 2014.

(Continued)

*Primary Examiner* — Ryan Severson
(74) *Attorney, Agent, or Firm* — Burns & Levinson LLP; Joseph M. Maraia

(57) ABSTRACT

The disclosure provides examples of an open architecture anchor for securing soft tissue to bone, for example, to repair a torn rotor cuff. The anchor includes at least one open helical coil defining a polygonal internal volume and at least one rib disposed within the polygonal internal volume and connected to at least two turns of the at least one open helical coil. The at least one rib is sized to engage a driver and a combination of the at least one rib and the polygonal internal volume is sized to provide an anchor drive torque required to drive the anchor into bone.

8 Claims, 7 Drawing Sheets

(56) References Cited

U.S. PATENT DOCUMENTS

| | | |
|---|---|---|
| 4,653,489 A | 3/1987 | Tronzo |
| 4,741,651 A | 5/1988 | Despres |
| 4,834,757 A | 5/1989 | Brantigan |
| 4,854,311 A | 8/1989 | Steffee |
| 4,913,143 A | 4/1990 | Oloff et al. |
| 4,961,740 A | 10/1990 | Ray et al. |
| 5,026,373 A | 6/1991 | Ray et al. |
| 5,055,104 A | 10/1991 | Ray |
| 5,116,337 A | 5/1992 | Johnson |
| 5,129,904 A | 7/1992 | Illi |
| 5,129,906 A | 7/1992 | Ross et al. |
| 5,197,967 A | 3/1993 | Wilson |
| 5,236,431 A | 8/1993 | Gogolewski et al. |
| 5,242,447 A | 9/1993 | Borzone |
| 5,354,299 A | 10/1994 | Coleman |
| 5,364,400 A | 11/1994 | Rego, Jr. et al. |
| 5,383,878 A | 1/1995 | Roger et al. |
| 5,407,427 A | 4/1995 | Zhu et al. |
| 5,411,523 A | 5/1995 | Goble |
| 5,447,533 A | 9/1995 | Vachon et al. |
| 5,464,427 A | 11/1995 | Curtis et al. |
| 5,470,334 A | 11/1995 | Ross et al. |
| 5,531,780 A | 7/1996 | Vachon |
| 5,571,139 A | 11/1996 | Jenkins, Jr. |
| 5,593,409 A | 1/1997 | Michelson |
| 5,609,635 A | 3/1997 | Michelson |
| 5,626,613 A | 5/1997 | Schmieding |
| 5,645,547 A | 7/1997 | Coleman |
| 5,658,285 A | 8/1997 | Marnay et al. |
| 5,676,545 A | 10/1997 | Jones |
| 5,681,352 A | 10/1997 | Clancy, III et al. |
| 5,688,285 A | 11/1997 | Yamada |
| 5,695,497 A | 12/1997 | Stahelin |
| 5,709,683 A | 1/1998 | Bagby |
| 5,802,794 A | 9/1998 | Robson |
| 5,833,715 A | 11/1998 | Vachon et al. |
| 5,888,227 A | 3/1999 | Cottle |
| 5,891,146 A | 4/1999 | Simon et al. |
| 5,921,982 A | 7/1999 | Lesh et al. |
| 5,951,560 A | 9/1999 | Simon et al. |
| 5,961,524 A | 10/1999 | Crombie |
| 5,964,783 A | 10/1999 | Grafton et al. |
| 5,968,047 A | 10/1999 | Reed |
| 5,968,098 A | 10/1999 | Winslow |
| 5,984,967 A | 11/1999 | Zdeblick et al. |
| 6,008,433 A | 12/1999 | Stone |
| 6,039,762 A | 3/2000 | McKay |
| 6,086,593 A | 7/2000 | Bonutti |
| 6,096,060 A | 8/2000 | Fitts et al. |
| 6,097,986 A | 8/2000 | Janke et al. |
| 6,196,780 B1 | 3/2001 | Wakai et al. |
| 6,235,057 B1 | 5/2001 | Roger et al. |
| 6,283,973 B1 | 9/2001 | Hubbard et al. |
| 6,360,129 B1 | 3/2002 | Ley et al. |
| 6,443,989 B1 | 9/2002 | Jackson |
| 6,447,545 B1 | 9/2002 | Bagby |
| 6,488,683 B2 | 12/2002 | Lieberman |
| 6,503,251 B1* | 1/2003 | Shadduck ............... 606/311 |
| 6,514,257 B2 | 2/2003 | Dovesi et al. |
| 6,517,542 B1 | 2/2003 | Papay et al. |
| 6,527,774 B2 | 3/2003 | Lieberman |
| 6,544,265 B2 | 4/2003 | Lieberman |
| 6,551,319 B2 | 4/2003 | Lieberman |
| 6,551,320 B2 | 4/2003 | Lieberman |
| 6,551,322 B1 | 4/2003 | Lieberman |
| 6,554,830 B1 | 4/2003 | Chappius |
| 6,589,245 B1 | 7/2003 | Weiler et al. |
| 6,626,917 B1 | 9/2003 | Craig |
| 6,685,728 B2* | 2/2004 | Sinnott et al. ............ 606/232 |
| 6,823,871 B2 | 11/2004 | Schmieding |
| 6,855,168 B2 | 2/2005 | Crozet |
| 6,863,671 B1 | 3/2005 | Strobel et al. |
| 6,953,462 B2 | 10/2005 | Lieberman |
| 7,033,372 B1 | 4/2006 | Cahalan |
| 7,070,586 B2 | 7/2006 | Hart et al. |
| 7,083,647 B1 | 8/2006 | Sklar et al. |
| 7,189,251 B2 | 3/2007 | Kay |
| 7,195,634 B2 | 3/2007 | Schmieding et al. |
| 7,217,279 B2 | 5/2007 | Reese |
| 7,322,986 B2 | 1/2008 | Wolf |
| 7,594,929 B2 | 9/2009 | Collette |
| 7,608,098 B1 | 10/2009 | Stone et al. |
| 7,867,252 B2 | 1/2011 | Criscuolo et al. |
| 7,914,539 B2 | 3/2011 | Stone et al. |
| 8,034,090 B2 | 10/2011 | Stone et al. |
| 8,636,799 B2 | 1/2014 | Sklar et al. |
| 8,672,967 B2 | 3/2014 | DiMatteo et al. |
| 2002/0022862 A1 | 2/2002 | Grafton et al. |
| 2002/0055737 A1 | 5/2002 | Lieberman |
| 2002/0055738 A1 | 5/2002 | Lieberman |
| 2002/0055742 A1 | 5/2002 | Lieberman |
| 2002/0087189 A1 | 7/2002 | Bonutti |
| 2002/0087190 A1 | 7/2002 | Benavitz et al. |
| 2002/0099382 A1 | 7/2002 | Salazar et al. |
| 2002/0143335 A1 | 10/2002 | von Hoffmann et al. |
| 2002/0165546 A1 | 11/2002 | Goble et al. |
| 2003/0055431 A1 | 3/2003 | Brannon |
| 2003/0065374 A1 | 4/2003 | Honeck |
| 2003/0069640 A1 | 4/2003 | Ferreira et al. |
| 2003/0125749 A1 | 7/2003 | Yuan et al. |
| 2003/0181913 A1 | 9/2003 | Lieberman |
| 2004/0015170 A1 | 1/2004 | Tallarida et al. |
| 2004/0030343 A1 | 2/2004 | Kurc |
| 2004/0039404 A1 | 2/2004 | Dreyfuss |
| 2004/0073216 A1 | 4/2004 | Lieberman |
| 2004/0097945 A1 | 5/2004 | Wolf |
| 2004/0122424 A1 | 6/2004 | Ferree |
| 2004/0143158 A1 | 7/2004 | Hart et al. |
| 2004/0143237 A1 | 7/2004 | Hart et al. |
| 2004/0267265 A1 | 12/2004 | Kyle |
| 2005/0107828 A1 | 5/2005 | Reese |
| 2005/0159727 A1 | 7/2005 | Lesh |
| 2005/0222681 A1 | 10/2005 | Richley et al. |
| 2005/0234458 A1 | 10/2005 | Huebner |
| 2005/0250984 A1 | 11/2005 | Lam et al. |
| 2005/0250985 A1 | 11/2005 | Saadat et al. |
| 2005/0250987 A1 | 11/2005 | Ewers et al. |
| 2005/0250988 A1 | 11/2005 | Ewers et al. |
| 2005/0283239 A1 | 12/2005 | Crozet |
| 2006/0009769 A1 | 1/2006 | Lieberman |
| 2006/0030948 A1 | 2/2006 | Manrique et al. |
| 2006/0079895 A1 | 4/2006 | McLeer |
| 2006/0100627 A1 | 5/2006 | Stone et al. |
| 2006/0106390 A1 | 5/2006 | Jensen et al. |
| 2006/0142769 A1 | 6/2006 | Collette |
| 2006/0149266 A1 | 7/2006 | Cordasco |
| 2006/0217681 A1 | 9/2006 | Hart et al. |
| 2006/0241636 A1 | 10/2006 | Novak et al. |
| 2006/0247642 A1 | 11/2006 | Stone et al. |
| 2006/0253080 A1 | 11/2006 | Tulleken et al. |
| 2006/0276841 A1 | 12/2006 | Barbieri et al. |
| 2007/0032797 A1 | 2/2007 | Ortiz et al. |
| 2007/0093895 A1 | 4/2007 | Donnelly et al. |
| 2007/0122764 A1 | 5/2007 | Balfour et al. |
| 2007/0142849 A1 | 6/2007 | Ewers et al. |
| 2007/0185532 A1 | 8/2007 | Stone et al. |
| 2007/0198019 A1 | 8/2007 | Schomer et al. |
| 2008/0027446 A1 | 1/2008 | Stone et al. |
| 2008/0065114 A1 | 3/2008 | Stone et al. |
| 2008/0082128 A1 | 4/2008 | Stone |
| 2008/0132932 A1 | 6/2008 | Hoeppner |
| 2008/0140092 A1 | 6/2008 | Stone et al. |
| 2008/0140093 A1 | 6/2008 | Stone et al. |
| 2008/0154314 A1 | 6/2008 | McDevitt |
| 2008/0179839 A1 | 7/2008 | Walters |
| 2009/0024174 A1 | 1/2009 | Stark |
| 2009/0042951 A1 | 2/2009 | Danziger |
| 2009/0076544 A1 | 3/2009 | DiMatteo et al. |
| 2009/0248029 A1 | 10/2009 | Paulos |
| 2009/0319043 A1 | 12/2009 | McDevitt et al. |
| 2011/0224727 A1 | 9/2011 | Housman et al. |
| 2011/0282450 A1 | 11/2011 | Donnelly et al. |
| 2011/0319933 A1 | 12/2011 | Tepic |
| 2012/0179163 A1 | 7/2012 | Housman et al. |

(56) References Cited

U.S. PATENT DOCUMENTS

| | | |
|---|---|---|
| 2013/0150859 A1 | 6/2013 | Kehres et al. |
| 2013/0158596 A1 | 6/2013 | Miller et al. |
| 2013/0158597 A1 | 6/2013 | Hernandez |
| 2013/0158598 A1 | 6/2013 | Lizardi |
| 2013/0158599 A1 | 6/2013 | Hester et al. |
| 2013/0158610 A1 | 6/2013 | Hernandez |
| 2014/0142697 A1 | 5/2014 | Sklar et al. |
| 2014/0148850 A1 | 5/2014 | DiMatteo et al. |

FOREIGN PATENT DOCUMENTS

| | | |
|---|---|---|
| CN | 101573078 A | 11/2009 |
| EP | 0538895 A2 | 4/1993 |
| EP | 0682917 B1 | 11/1995 |
| EP | 0502698 B1 | 11/1997 |
| EP | 0669110 B1 | 5/2000 |
| EP | 1147751 B1 | 10/2001 |
| EP | 1093774 B1 | 6/2002 |
| EP | 0796593 B1 | 5/2004 |
| EP | 1917926 A1 | 5/2008 |
| EP | 2036501 A3 | 3/2009 |
| EP | 2422711 A2 | 2/2012 |
| EP | 2422712 A2 | 2/2012 |
| EP | 2596758 A1 | 5/2013 |
| EP | 2601894 A1 | 6/2013 |
| FR | 2760355 A1 | 9/1998 |
| FR | 2803739 A1 | 7/2001 |
| FR | 2846867 A1 | 5/2004 |
| JP | H10200 A | 1/1998 |
| WO | 9608205 A1 | 3/1996 |
| WO | 9619947 A1 | 7/1996 |
| WO | 9802117 A1 | 1/1998 |
| WO | 9826717 A1 | 6/1998 |
| WO | 2006055516 A2 | 5/2006 |
| WO | 2007093192 A1 | 8/2007 |
| WO | 2008021474 A2 | 2/2008 |
| WO | 20081009944 A1 | 8/2008 |
| WO | 2009042951 A1 | 4/2009 |
| WO | 2010017631 A1 | 2/2010 |
| WO | 2011112776 A1 | 9/2011 |
| WO | 2012171011 A1 | 12/2012 |

OTHER PUBLICATIONS

International Search and Written Opinion for PCT/US2014/022539 mailed Jun. 27, 2014.

International Search and Written Opinion for PCT/US2014/020747 mailed Jun. 6, 2014.

Decision of Rejections for Japanese Patent Application No. 2011-538642, mailed Jun. 2, 2014.

Hunt, Patrick, D.V.M. et al. "Development of a Perforated Biodegradable Interference Screw", Arthroscopy: The Journal of Arthroscopic and Related Surgery, vol. 21, No. 3, Mar. 2005; pp. 258-265.

International Search and Written Opinion for PCT/US2011/027837 mailed May 19, 2011.

Smith & Nephew brochure titled "Bio RCITM Bioabsorbable Screws: Anatomically Targeted Screws for ACL and PCL Reconstruction", 2000.

Biomet brochure "Bio-CoreTM Interference Screw", 2007.

International Search and Written Opinion for PCT/US2009/065304 mailed Jun. 5, 2013.

International Search and Written Opinion for PCT/US2012/041298 mailed Jun. 5, 2013.

International Search and Written Opinion for PCT/US2012/028803 mailed Oct. 24, 2010.

Notice of Reasons for Rejections for Japanese Patent Application No. 2011-538642, mailed Oct. 1, 2013.

First Office Action for Chinese Patent Application No. 200980155954.7, issued Apr. 12, 2013.

Second Office Action for Chinese Patent Application No. 200980155954.7, issued Oct. 24, 2013.

First Office Action for Chinese Patent Application No. 201180013194.3 issued Jul. 21, 2014.

Notice of Reasons for Rejection for Japanese Patent Application No. 2012-557236 mailed Nov. 25, 2014.

Patent Examination Report No. 1 for Australian Patent Application No. 20093198796 issued Nov. 10, 2014.

International Search and Written Opinion for PCT/US2014/066389 mailed Feb. 17, 2015.

Notice of Reasons for Rejection for Japanese Patent Application No. 2012-557236 mailed Mar. 2, 2015.

Patent Examination Report No. 1 for Australian Patent Application No. 2011224326 issued Apr. 21, 2015.

Second Office Action for Chinese Patent Application No. 201180013194.3, issued Mar. 23, 2015.

First Office Action for Chinese Patent Application No. 201280022627.6, issued Apr. 13, 2015.

\* cited by examiner

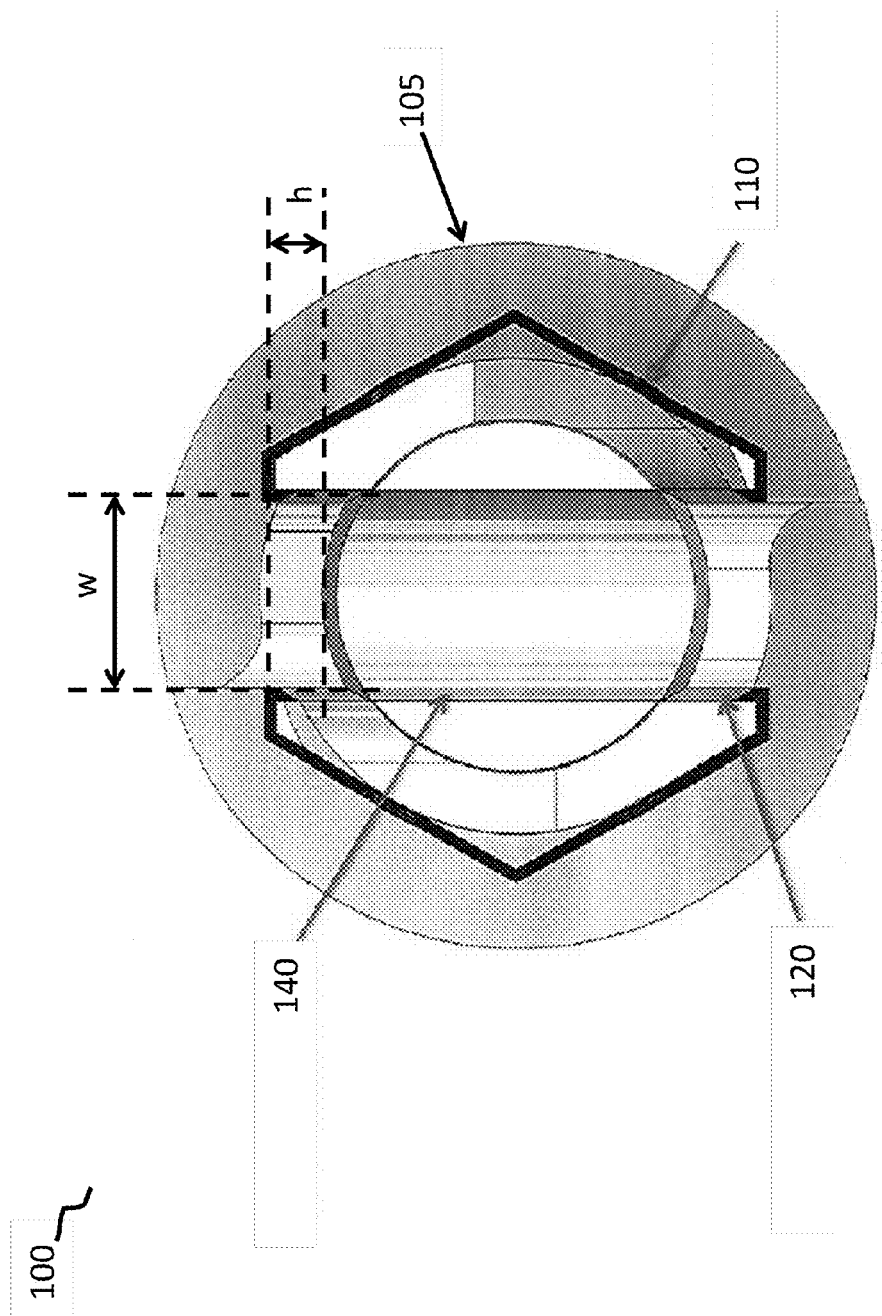

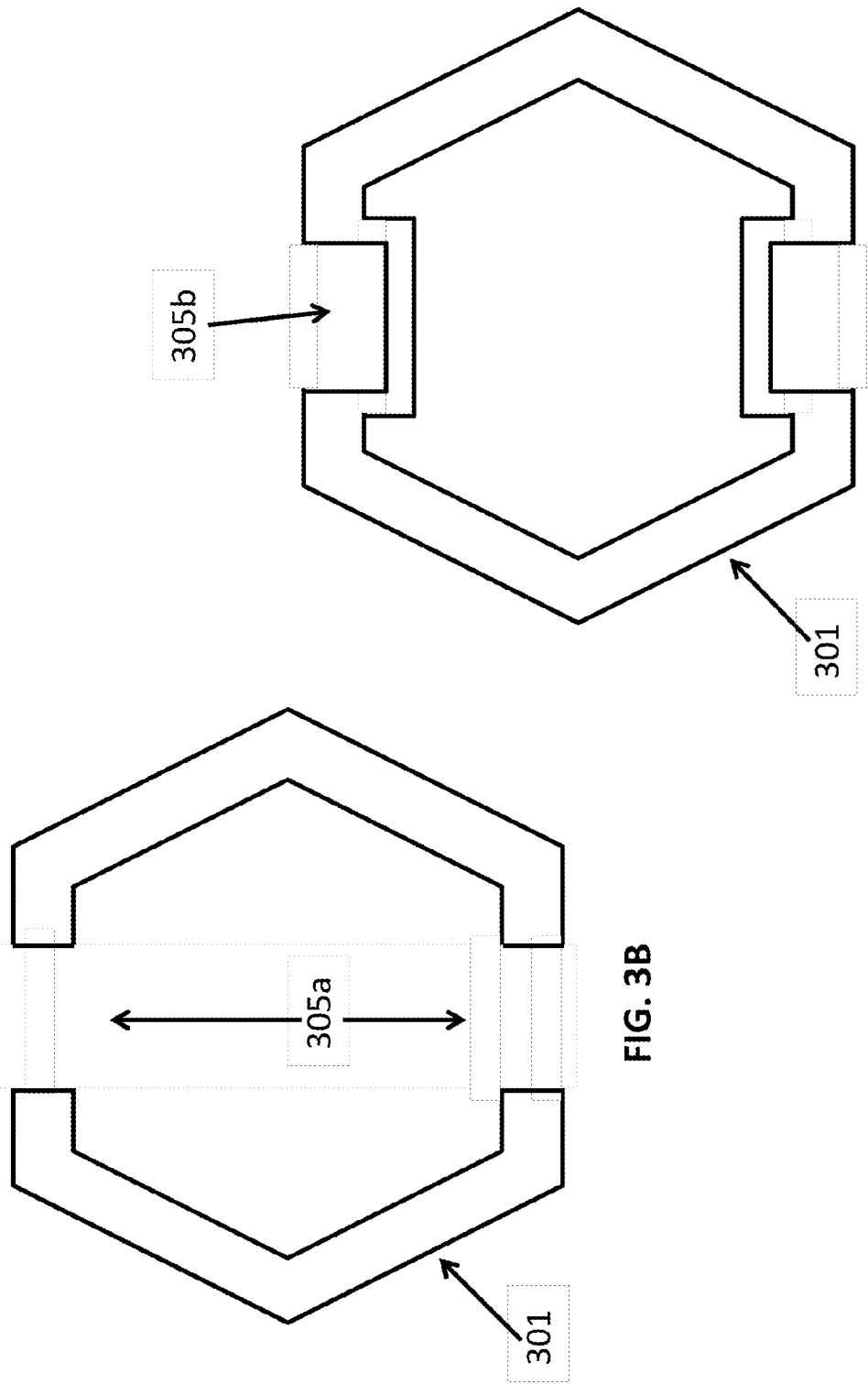

MINIATURIZED DUAL DRIVE OPEN ARCHITECTURE SUTURE ANCHOR

BACKGROUND

Arthroscopic surgery is a minimally invasive surgical procedure in which an examination and sometimes treatment of damage of the interior of a joint is performed using an arthroscope, a type of endoscope that is inserted into the joint through a small incision. Arthroscopic procedures, such as repairing a torn rotor cuff, often require soft tissue to be reattached to bone. To achieve this, anchors (sometimes called "suture anchors") are placed in the bone and sutures attached to the anchor are passed through the tissue to securely retain the tissue in place.

SUMMARY

To reduce the amount of bone stock removed by an anchor and minimize invasiveness, ever smaller open architecture anchors are being used. However, smaller open architecture anchors result in a problematic tradeoff between reduced interior volume of the anchor and weakened drive support structure. In order to maintain structural integrity during screw-in insertion, drive elements must be capable of withstanding the torsion required for insertion of the anchor. Drive ribs are typically provided within an internal volume of an anchor to provide a structural element for a driver to apply torsion during insertion. However, as the size of the anchor is reduced, drive ribs of adequate depth/size to drive an anchor begin to occlude internal suture passages. A need therefore exists for a drive support structure to be capable of withstanding torsional drive forces during anchor insertion and to have a sufficiently small profile to avoid occlusion of internal suture passages.

The foregoing needs are addressed by an open architecture anchor having a dual drive system using both drive ribs and an internal polygonal (e.g., hexagon, octagon, square, or any other regular or irregular polygon) drive feature. This new dual drive feature allows the anchor to withstand torsional drive forces while including drive ribs of a reduced size. The internal volume of the anchor thereby is maintained such that adequate cross-sectional area is provided for the passage of sutures through the anchor and/or driver. Using a smaller anchor allows for preservation of bone stock and more rapid healing.

Accordingly, in one aspect, at least one embodiment described herein relates to an anchor for securing soft tissue to bone, for example, to repair a torn rotator cuff. The anchor includes at least one open helical coil defining a polygonal internal volume communicating with a region exterior to the at least one open helical coil through a spacing between turns of the at least one open helical coil, wherein the polygonal internal volume is sized to engage a driver. The anchor also includes at least one rib disposed within the polygonal internal volume and connected to at least two turns of the at least one open helical coil, wherein the at least one rib is sized to engage the driver and a combination of the at least one rib and the polygonal internal volume is sized to provide an anchor drive torque required to drive the anchor into bone.

Any of the embodiments described herein can include one or more of the following embodiments. In some embodiments the polygonal internal volume further comprises a cross-sectional shape including at least one of a regular polygon; irregular polygon; square, rectangle, triangle, hexagon, and/or octagon. In some embodiments, the at least one rib includes a first rib positioned on a first side of the polygonal internal volume and a second rib positioned on a second side of the polygonal internal volume. In some embodiments, the anchor also includes a suture bridge affixed to and disposed within a distal end of the anchor. In some embodiments, the at least one open helical coil is a dual lead helical coil.

In another aspect, at least one embodiment described herein provides a tissue repair system. The system includes a driver comprising a handle and a polygonal shaft connected to the handle, at least part of the polygonal shaft having a polygonal-shaped cross-section, the polygonal shaft including a distal end having at least one groove extending toward a proximal end of the polygonal shaft. The system also includes an anchor engageable with a distal end of the driver. The anchor includes at least one open helical coil defining a polygonal internal volume communicating with a region exterior to the at least one open helical coil through a spacing between turns of the at least one open helical coil, wherein the polygonal internal volume is sized to engage the polygonal shaft of the driver. The anchor also includes at least one rib disposed within the polygonal internal volume and connected to at least two turns of the at least one open helical coil, wherein the at least one rib is sized to engage the at least one groove of the driver and a combination of the at least one rib and the polygonal internal volume is sized to provide an anchor drive torque required for the driver to drive the anchor into bone.

The anchors and systems for tissue repair described herein (hereinafter "technology") can provide one or more of the following advantages. One advantage of the technology is that a smaller open architecture anchor can be provided by including a polygonal internal volume and reduced profile drive ribs. The combination of the polygonal internal volume and reduced profile drive ribs can advantageously distribute a torsional drive force, thereby maintaining structural integrity during insertion of the anchor into bone despite the reduced size and load capability of the reduced profile drive ribs. The reduced profile drive ribs advantageously allow for smaller open architecture anchors to maintain sufficiently large internal suture passages to pass one or more sutures. The open architecture of the technology advantageously allows for bony ingrowth, thereby reducing patient recovery time. The reduced size of the open architecture advantageously preserves bone stock, thereby preserving bone integrity and reducing patient recovery time. The reduced size of the open architecture also advantageously allows a higher percentage of the diameter of the anchor to be dedicated to thread depth, thereby improving fixation strength of the anchor in the bone.

Further areas of applicability of the present disclosure will become apparent from the detailed description provided hereinafter. It should be understood that the detailed description and specific examples are intended for purposes of illustration only and are not intended to limit the scope of the disclosure.

BRIEF DESCRIPTION OF THE DRAWINGS

The foregoing and other objects, features, and advantages will be apparent from the following more particular description of the embodiments as illustrated in the accompanying drawings in which like reference characters refer to the same parts throughout the different views. The drawings are not necessarily to scale, emphasis instead being placed upon illustrating the principles, characteristics, and features of the embodiments. In the drawings:

FIG. 1A is an end view of a proximal end of an example open architecture anchor in accordance with various embodiments.

FIGS. 3B and 3C are a cross-sectional views of alternative distal ends of the example anchor driver of FIG. 3A in accordance with various embodiments.

DETAILED DESCRIPTION

The following description of examples is in no way intended to limit the disclosure, its application, or uses.

Figure 1B:
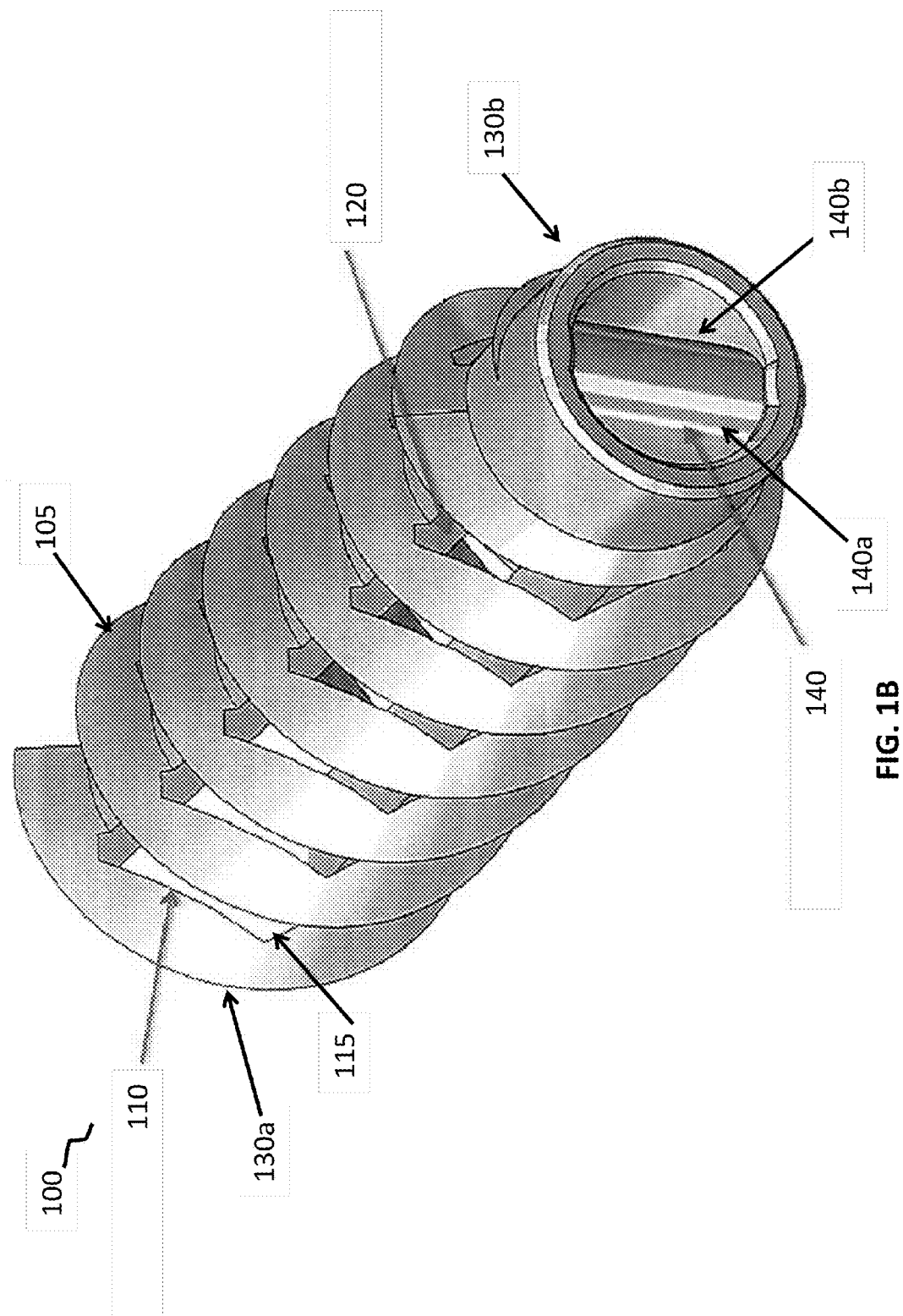
FIG. 1B is an isometric view of the example open architecture anchor of FIG. 1 in accordance with various embodiments.
Figure 1C:
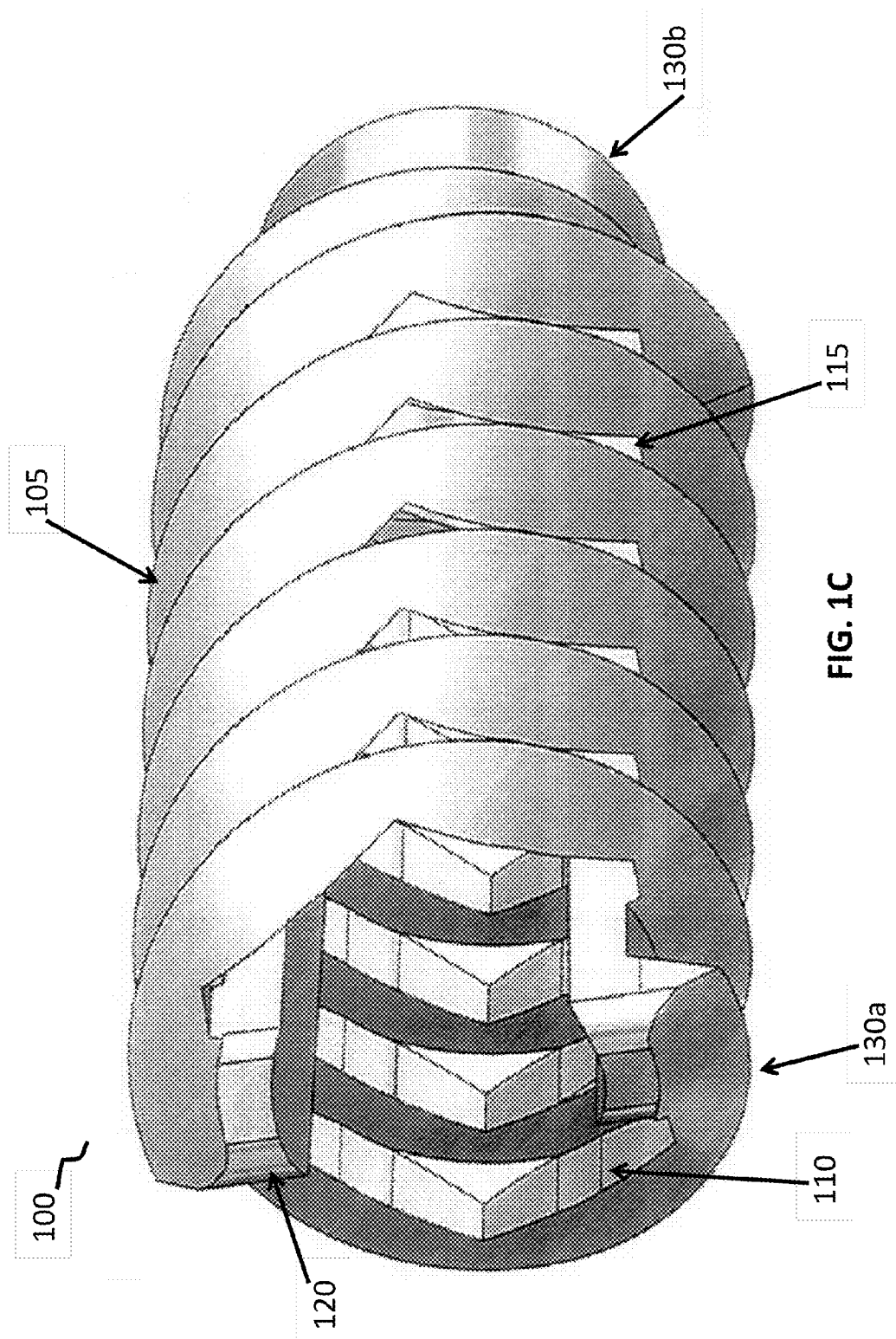
FIG. 1C is second isometric view of the example open architecture anchor of FIG. 1 in accordance with various embodiments.
Figure 3A:
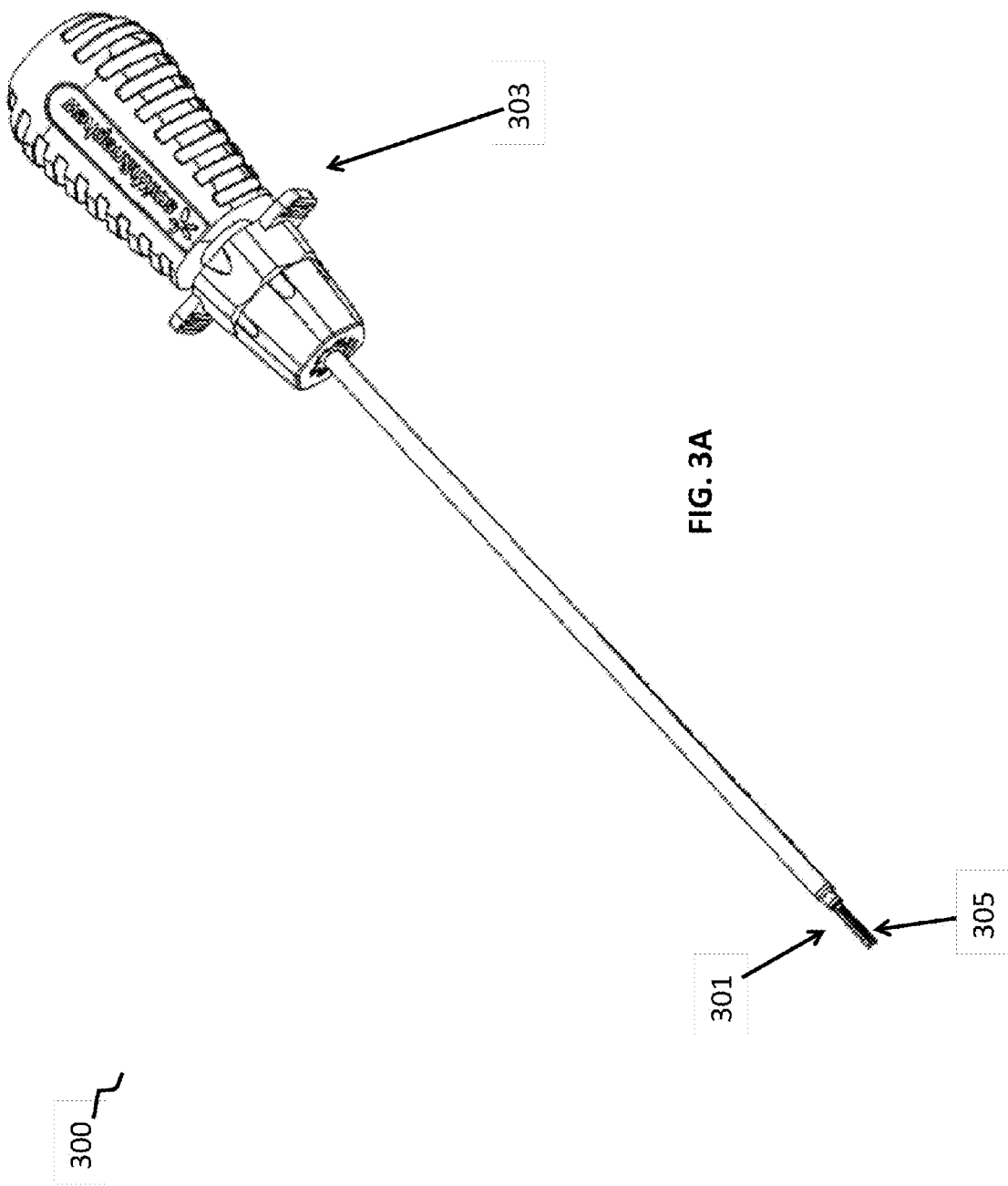
FIG. 3A is an isometric view of an example anchor driver in accordance with various embodiments.

FIGS. 1A-1C show an example of an anchor 100 including at least one (open) helical screw thread 105. The helical screw thread 105 defines a polygonal internal volume 110 (e.g., hexagonal as shown). The polygonal internal volume 110 communicates with a region exterior to the at least one open helical coil screw 105 through a spacing 115 between turns of the helical screw thread 105. The polygonal internal volume 110 engages a corresponding polygonal shaft of an anchor driver (e.g., polygonal shaft 301 of anchor driver 300 as shown in FIGS. 3A-3B).

In use, the anchor 100 is located at a distal end of the anchor driver such that the polygonal shaft engages the polygonal internal volume of the anchor 100. A torsional drive force is then applied to the anchor 100 by the anchor driver to insert the anchor 100 into bone. In various embodiments, the anchor driver can engage the polygonal internal volume 110 along only a portion of the longitudinal length of the anchor (i.e., from proximal end 130a to distal end 130b). Engagement of substantially the entire length of the polygonal internal volume 110 by the anchor driver, in accordance with various embodiments, can be advantageous because the torsional drive force applied to the anchor 100 during insertion can be distributed throughout the length of the anchor 100, rather than concentrated on a smaller portion of the anchor 100. After the anchor 100 is inserted into bone and the patient begins to heal, new bone grows into the internal volume 110 through the spacing 115. For faster and more complete healing, this "bony ingrowth" is highly desirable.

In another embodiment, the anchor 100 further includes at least one rib 120 (e.g., two as shown) connected to at least two turns of the helical screw thread 105. The ribs 120 engage corresponding grooves of an anchor driver (e.g., grooves 305 of anchor driver 300 as shown in FIGS. 3A-3B). In use, the anchor 100 is located at a distal end of the anchor driver such that the grooves engage the ribs 120 of the anchor 100. In various embodiments, a surgeon inserts the anchor 100 into bone using the anchor driver by applying a torsional drive force to the driver, which transmits the torsion to the anchor 100, thereby screwing the anchor into bone.

In various embodiments, engagement of the anchor driver with both the polygonal internal volume 110 and the ribs 120 of the anchor 100 advantageously distributes the torsional drive force between the ribs 120 and the polygonal internal volume 110. Such load distribution, in various embodiments, will allow the anchor 100 to withstand the torsional drive force despite having undersized drive ribs 120. For example, ribs 120 having a width (w) and/or height (h) too small to independently support the torsional drive force can be used in combination with a polygonal internal volume 110 to establish the necessary structural properties of the anchor 100. In various embodiments, the anchor driver can engage the polygonal internal volume 110 and/or the ribs 120 along only a portion of the longitudinal length of the anchor (i.e., from proximal end 130a to distal end 130b). However, engagement of substantially the entire length of the polygonal internal volume 110 and/or the ribs 120 by the anchor driver, in accordance with various embodiments, can be advantageous because the torsional drive force applied to the anchor 100 during insertion can be distributed throughout the length of the anchor 100, rather than concentrated on a smaller portion of the anchor 100. This further distribution allows further reduction in width (w) and/or height (h). The reduced width (w) and/or height (h) can, in various embodiments; advantageously prevent occlusion of a cross-sectional area of the polygonal internal volume 110 such that sutures can pass inside the anchor 100 and/or the anchor driver.

The anchor 100, in various embodiments, can also include a suture bridge 140 attached to and disposed at least partially within a distal end 130b of the anchor 100. The suture bridge 140 can be located entirely within the distal end 130b of the anchor 100 (e.g., as shown in FIG. 1B) but can also protrude distally from the distal end 130b. The suture bridge 140 can, in various embodiments, include a rounded distal-facing region around which one or more sutures can be routed. In such embodiments, a first end of each suture extends proximally through the anchor 100 on a first side of the suture bridge 140a and a second end of each suture extends proximally through the anchor 100 on a second side of the suture bridge 140b. The suture bridge 140 advantageously retains one or more sutures within the anchor 100 while preventing the cutting, pinching, and/or other weakening of the sutures associated with positioning the sutures between the anchor 100 and the bone.

Some examples of the anchor 100 include two helical screw threads 105 in a "dual lead" thread arrangement. Dual lead means that two "ridges" are wrapped around the anchor 100. The anchor 100 can be constructed from, for example but not limited to, polymers (e.g., polyetheretherketone), bioabsorbable materials, metals (e.g., surgical steel, titanium), or any other suitable material.

Figure 2B:
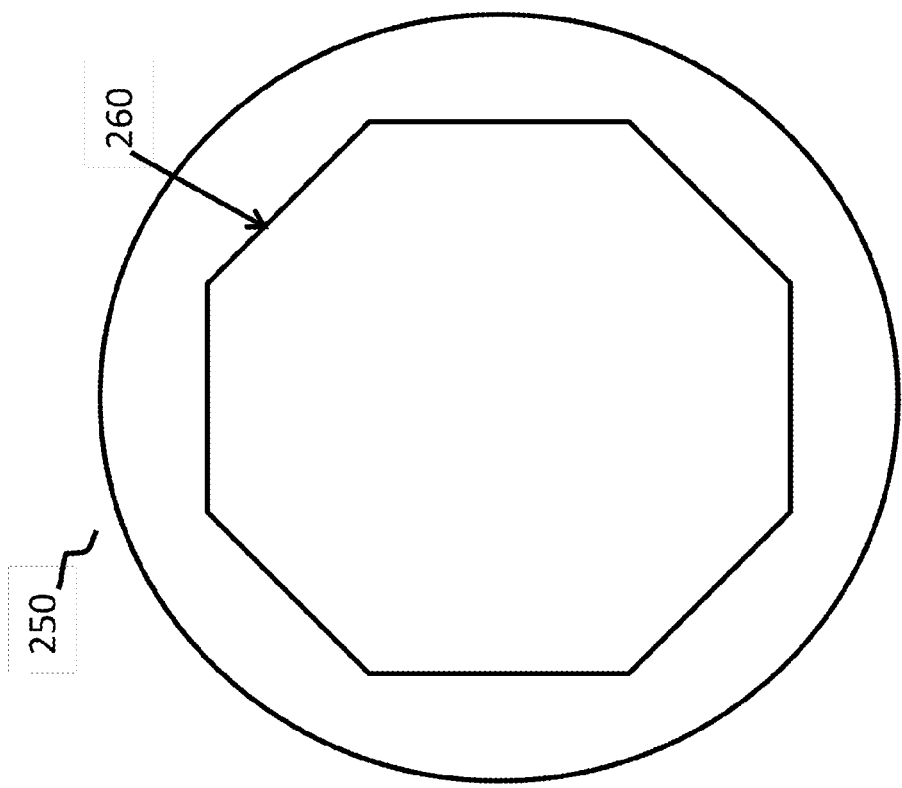
FIGS. 2A and 2B are cross-sectional views of a polygonal internal volume of alternative open architecture anchors in accordance with various embodiments, wherein the ribs have been omitted for clarity.
Figure 2A:
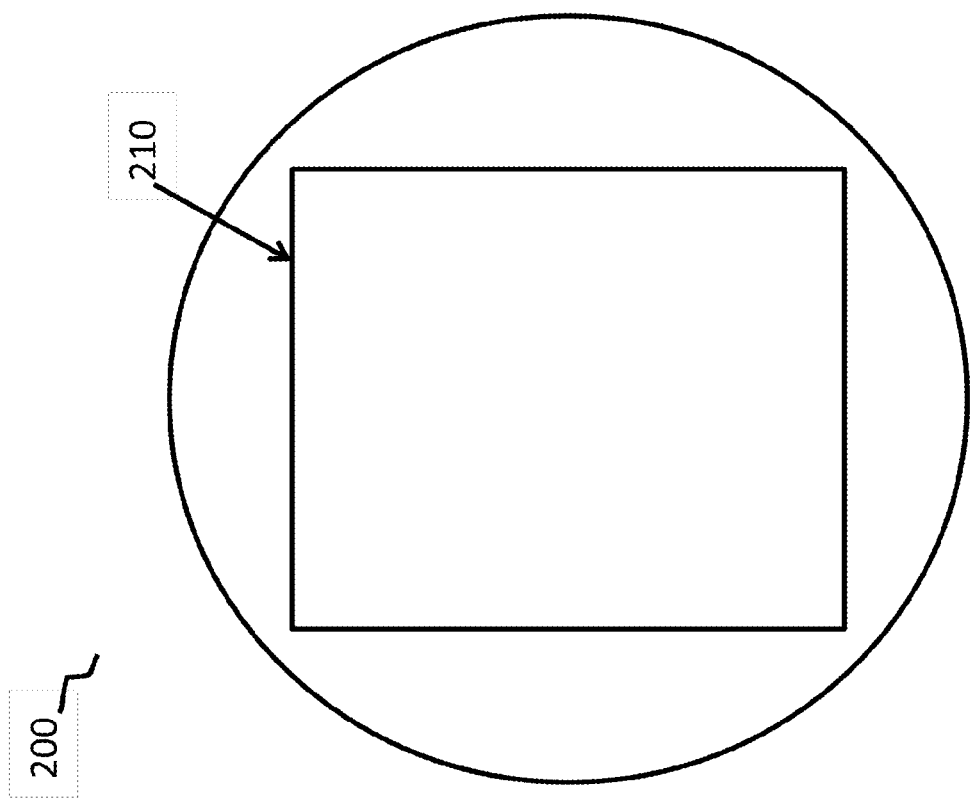

As shown in FIGS. 1A, 2A, and 2B, any regular polygonal or irregular polygonal shape can be used for the polygonal internal volume 110, 210, 260 of the anchor 100, 200, 250, respectively, in accordance with various embodiments. Shapes of the polygonal internal volume 110, 210, 260 can include, for example but are not limited to, a hexagon (e.g., the shape of internal volume 110 as shown in FIG. 1A), a rectangle (e.g., the shape of internal volume 210 as shown in FIG. 2A), an octagon (e.g., the shape of internal volume 260 as shown in FIG. 2B), a triangle, a star-shape, a trapezoid, and/or any other suitable non-circular shape capable of engaging with a driver to receive at least a portion of a transmitted torsional drive force.

FIGS. 3A-3C show an anchor driver 300 in accordance with various embodiments. The anchor driver includes a polygonal shaft 301 connected at a proximal end to a handle 303. The polygonal shaft 301 includes one or more grooves 305 (e.g., two as shown) extending toward a proximal end of the polygonal shaft 301. The polygonal shaft 301, in various embodiments, can have a polygonal-shaped cross-section along its entire longitudinal length. In various embodiments, the polygonal shaft 301 can have a polygonal-shaped cross section along only a portion of its longitudinal length and can have at least one different cross-sectional shape (e.g., a different polygon, a circle, an ellipse) along one or more additional portions of its longitudinal length.

As shown in FIG. 3B, the one or more grooves 305 can be provided, in various embodiments, as cut-out grooves 305a which are open to an interior of the polygonal shaft 301. As shown in FIG. 3C, the one or more grooves 305 can be provided, in various embodiments, as channel grooves 305b. As described above, in various embodiments, the polygonal shaft 301 can be inserted into the polygonal internal volume (e.g., 110 as described above) of an anchor (e.g., 100 as described above) to engage the polygonal shaft 301 with the polygonal internal volume and the grooves 305 with the ribs (e.g., 120 as described above).

In various embodiments, the handle 303 can be manufactured from a polymer material and via an injection molding process. However, any other suitable material (e.g., metals, composites, wood) and/or process (e.g., extrusion, machining, electro-chemical machining) can be used. The polygonal shaft 301 and/or any surfaces defining a groove 305 thereon can be made from a metal material via an extrusion or drawing process. However, any other suitable material (e.g., plastics, composites) and/or process (e.g., injection molding, casting, machining, electro-chemical machining) can be used. The polygonal shaft 301 can be coupled to the handle 303 via an interference fit. However, any other suitable method of coupling (e.g., screws, adhesives, rivets) can be used.

Figure 4:
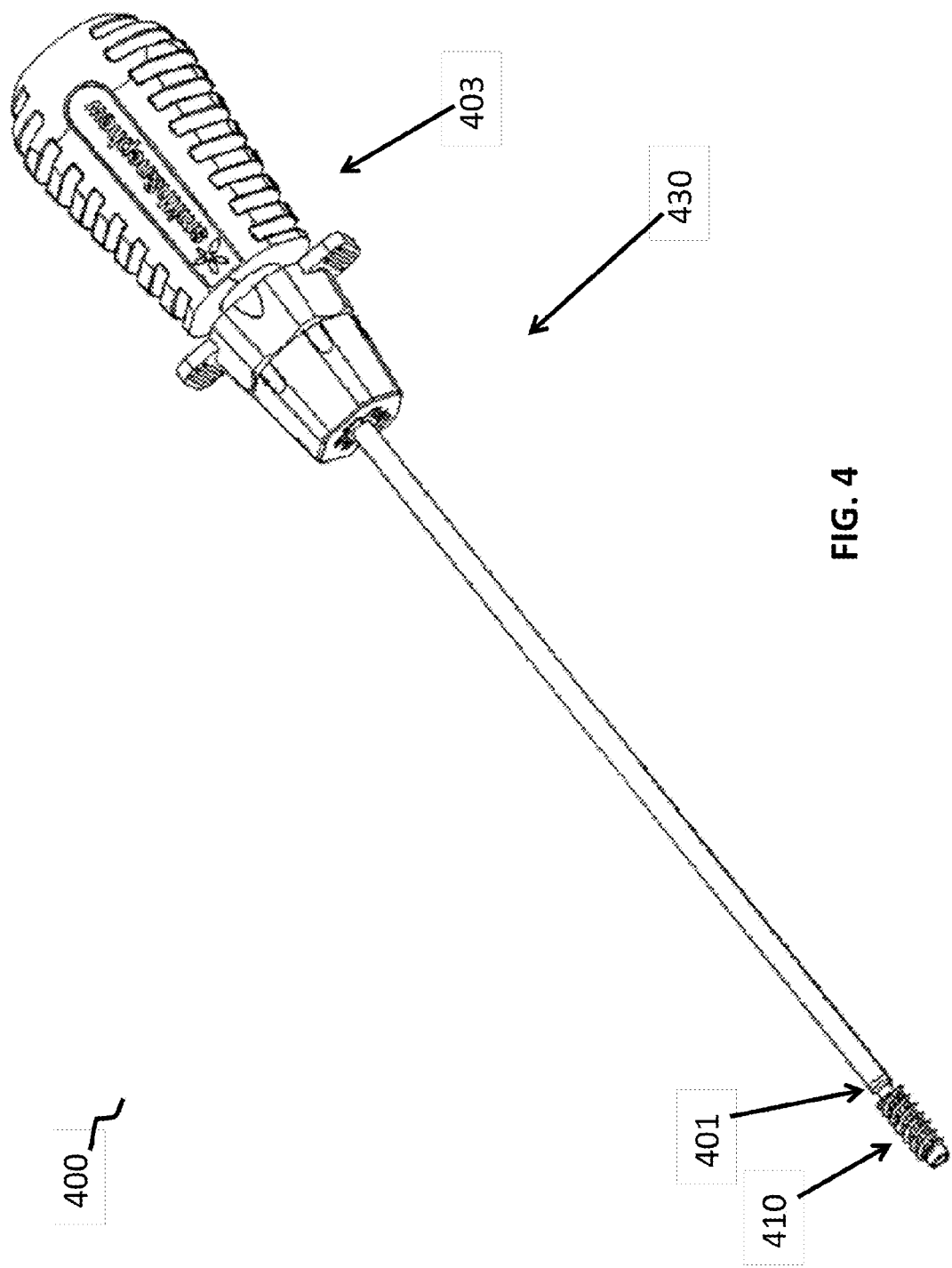
FIG. 4 is an isometric view of an example tissue fixation system in accordance with various embodiments.

FIG. 4 illustrates a tissue fixation system 400 in accordance with various embodiments. The tissue fixation system 400 includes an anchor 410 engaged with a driver 430. In various embodiments, one or more sutures (not shown) can be installed such that each suture passes around a suture bridge (e.g., 140 as shown in FIG. 1) and the ends of each suture extend toward a proximal end of the tissue fixation system 400 through the anchor 410, a grooved polygonal shaft 401 of the anchor driver 430, and/or a handle 403 of the anchor driver 430. In various embodiments, a surgeon can apply a torsional drive force to the handle 403, which transmits the torsional drive force to the grooved polygonal shaft 401 thereby applying the torsional drive force to the anchor 410 to screw the anchor 410 into bone. In various embodiments, the anchor 410 may include, for example but not limited to, any anchor 100, 200, 250 as described hereinabove with reference to FIGS. 1A-1C and FIGS. 2A-2B. In various embodiments, the anchor driver 430, the handle 403, and/or the grooved polygonal shaft 401 may include, for example but not limited to, any anchor driver 300, any polygonal shaft 301, any grooves 305, 305a, 305b, and/or any handle 303 as described hereinabove with reference to FIGS. 3A-3C.

As various modifications could be made in the constructions and methods herein described and illustrated without departing from the scope of the invention, it is intended that all matter contained in the foregoing description or shown in the accompanying drawings shall be interpreted as illustrative rather than limiting. Thus, the breadth and scope of the present invention should not be limited by any of the above-described examples, but should be defined only in accordance with the following claims appended hereto and their equivalents.

What is claimed is:

1. An anchor comprising:
    at least one open helical coil defining a polygonal internal volume communicating with a region exterior to the at least one open helical coil through a spacing between turns of the at least one open helical coil, wherein the polygonal internal volume is defined by at least three sides of the at least one open helical coil, each of the at least three sides joined together at an angle, the polygonal internal volume sized to engage a driver; and
    at least one rib extending from at least one of the at least three sides of the at least one open helical coil into the polygonal internal volume and connected to at least two turns of the at least one open helical coil, the at least one rib sized to engage the driver, and a combination of the at least one rib and the polygonal internal volume is sized to provide an anchor drive torque required to drive the anchor into bone.

2. The anchor of claim 1, wherein the polygonal internal volume further comprises a cross-sectional shape including at least one of a regular polygon, irregular polygon, ellipse, square, rectangle, triangle, hexagon, and/or octagon.

3. The anchor of claim 1, wherein the at least one rib includes a first rib extending from one of the at least three sides of the at least one open helical coil into the polygonal internal volume and a second rib extending from another one of the at least three sides of the at least one open helical coil into the polygonal internal volume.

4. The anchor of claim 1, further comprising a suture bridge affixed to and disposed within a distal end of the anchor.

5. The anchor of claim 1 wherein the at least one open helical coil is a dual lead helical coil.

6. The anchor of claim 1 wherein the at least one rib sized to engage the driver comprises the at least one rib sized to engage at least one groove of the driver.

7. A tissue repair system comprising:
    a driver comprising a handle and a polygonal shaft connected to the handle, at least part of the polygonal shaft having a polygonal-shaped cross-section, the polygonal shaft including a distal end having at least one groove extending toward a proximal end of the polygonal shaft; and
    an anchor engageable with a distal end of the driver comprising:
        at least one open helical coil defining a polygonal internal volume communicating with a region exterior to the at least one open helical coil through a spacing between turns of the at least one open helical coil, wherein the polygonal internal volume is defined by at least three sides of the at least one open helical coil, each of the at least three sides joined together at an angle, the polygonal internal volume sized to engage a driver; and
        at least one rib extending from at least one of the at least three sides of the at least one open helical coil into the polygonal internal volume and connected to at least two turns of the at least one open helical coil, the at least one rib sized to engage the driver, and a combination of the at least one rib and the polygonal internal volume is sized to provide an anchor drive torque required to drive the anchor into bone.

8. The tissue repair system of claim 7, wherein the at least one rib sized to engage the driver comprises the at least one rib sized to engage the at least one groove of the driver.

* * * * *